United States Patent [19]

Baskeyfield et al.

[11] Patent Number: 5,607,662
[45] Date of Patent: Mar. 4, 1997

[54] PHARMACEUTICAL INHALATION COMPOSITIONS

[75] Inventors: Lewis J. Baskeyfield; Graham F. Jay, both of Cheshire; Paul Wright, Nottinghamshire, all of England

[73] Assignee: Fisons, PLC, Great Britain

[21] Appl. No.: 295,853

[22] PCT Filed: Mar. 10, 1993

[86] PCT No.: PCT/GB93/00503

§ 371 Date: Dec. 27, 1994

§ 102(e) Date: Dec. 27, 1994

[87] PCT Pub. No.: WO93/17663

PCT Pub. Date: Sep. 16, 1993

[30] Foreign Application Priority Data

Mar. 10, 1992 [GB] United Kingdom .................. 9205183
Mar. 17, 1992 [GB] United Kingdom .................. 9205738
Mar. 17, 1992 [GB] United Kingdom .................. 9205739

[51] Int. Cl.$^6$ ........................................ A61K 9/14
[52] U.S. Cl. ..................... 424/46; 424/434; 424/435
[58] Field of Search ................... 424/129, 46, 434, 424/435

[56] References Cited

U.S. PATENT DOCUMENTS 5,254,330 10/1993 Ganderton et al. ................ 424/46

FOREIGN PATENT DOCUMENTS 0365119 4/1990 European Pat. Off. .
WO88/08304 11/1988 WIPO .
WO91/11179 8/1991 WIPO .

Primary Examiner—Nathan M. Nutter
Attorney, Agent, or Firm—Nixon, Hargrave, Devans & Doyle

[57] ABSTRACT

A non-pressurized pharmaceutical inhalation composition includes a therapeutically effective amount of a particulate inhalation medicament. The medicament has a mass median diameter in the range 0.01 to 15 μm. A particulate polysaccharide entrapped flavoring agent is included in the composition and has a mass median diameter in the range of 10 to 200 μm. The composition can be used to practice a method for treatment of reversible obstructive airway disease which includes administering the pharmaceutical composition to a patient.

10 Claims, No Drawings

PHARMACEUTICAL INHALATION COMPOSITIONS

This invention relates to pharmaceutical compositions for administration by inhalation, more particularly to non-pressurised powder compositions.

Many medicaments, especially those for the treatment of diseases of the respiratory tract, are administered by inhalation. However, some medicaments, such as reproterol hydrochloride, have an undesirable taste when administered by inhalation, this being due to that proportion of medicament which is; deposited in the mouth and throat of the patient. Thus, it would be desirable to modify the taste of inhalation compositions by incorporating a flavouring agent, as this may result in improved patient compliance especially if the patients are young children.

Medicaments for inhalation are commonly administered in the form of powders, either from pressurised canisters containing the powder in admixture with a liquefied gas aerosol propellant, or as non-pressurised dry powder compositions.

In the former case it is known to include flavouring and/or sweetening agents in the composition to improve the taste of the composition and/or to give the composition a recognisable flavour so that the patient realises when a dose has been inhaled, as disclosed in EP-A-365119. However, such compositions suffer from the disadvantage that the propellant may comprise a chlorofluorocarbon (CFC) which is thought to be harmful to the environment generally and the ozone layer in particular. Furthermore, the flavouring agent may be inhaled into the lung.

It would be desirable to incorporate flavouring agents into non-pressurised dry powder pharmaceutical compositions. However, flavouring agents usually exist as oils or sticky solids at room temperature. This renders them unsuitable for use in dry powder formulations, for example, because they have poor flow properties and could cause the powdered medicament to agglomerate thus reducing dispersion to the lung.

We now provide a pharmaceutical inhalation composition which overcomes or substantially mitigates these disadvantages.

We have now found that by entrapping the flavouring agent in a polysaccharide, the flavouring agent may be kept sufficiently free flowing to be incorporated into non-pressurised powder inhalation compositions.

Thus, according to the invention, we provide a non-pressurised pharmaceutical inhalation composition comprising a therapeutically effective amount of a particulate inhalation medicament having a mass median diameter in the range 0.01 to 15 μm and a particulate polysaccharide entrapped flavouring agent having a mass median diameter in the range 10 to 200 μm.

Polysaccharide entrapped flavouring agents are known for use in the food industry. In addition to the flavouring agent and polysaccharide, food flavourings generally contain other excipients, for example emulsifying agents, e.g. acacia gum which is the gummy exudate from the stem and branches of *Acacia senegal* and other species of Acacia. However, we have found that the presence of excipients, such as emulsifying agents, may cause the polysaccharide entrapped flavouring agent to be sticky or otherwise render it unsuitable for use in non-pressurised pharmaceutical inhalation compositions. Therefore, we prefer the particulate polysaccharide entrapped flavouring agents used in the compositions according to the invention to contain a minimum amount of, and preferably no, excipients in addition to the flavouring agent and polysaccharide.

Any conventional pharmaceutically acceptable flavouring agents may be used, particular flavouring agents which may be mentioned include volatile oils, e.g. peppermint oil; and menthol. The proprietary product known by the tradename DENTOMINT™ flavouring agent, which contains both peppermint oil and menthol, may also be used. We prefer the flavouring agent to be peppermint oil BP/Ph. Eur.

Polysaccharides in which the flavouring agent is entrapped include, for example, polyglucoses. We prefer the polysaccharide to be a dextran or a dextrin. We particularly prefer the polysaccharide to be a dextrin, especially maltodextrin. Dextrins such as maltodextrin may be prepared from a variety of sources, such as starches, e.g. maize, corn, wheat, rice, rye, oats, pea, tapioca or potato starch.

The molecular weight of the polysaccharide must be high enough to ensure adequate entrapment of the flavouring agent. The molecular weight may vary, but is preferably from 500 to 1,000,000, more preferably from 500 to 250,000, and especially from 500 to 20,000.

The flavouring agent may be entrapped in the polysaccharide by atomisation of a mixture of a solution of the polysaccharide and the flavouring agent. Any suitable form of atomiser can be used. Atomisation results from an energy source acting on liquid bulk. Resultant forces build up to a point where liquid break-up and disintegration occurs and individual spray droplets are created. The different atomisation techniques available concern the different energy forms applied to the liquid bulk. Common to all atomisers is the use of energy to break-up liquid bulk. Centrifugal, pressure and kinetic energy are used in common forms of atomiser. Sonic and vibratory atomisers are also used. Specific atomisers which may be mentioned include rotary atomisers, e.g. those involving veined wheels, vaneless discs, cups, bowls and plates; pressure atomisers, e.g. those involving pressure nozzles, centrifugal pressure nozzles, swirl chambers and grooved cores; kinetic energy or pneumatic atomisers, e.g. those involving two or three fluids, or internal or external mixing; and sonic energy nozzles, e.g. involving sirens or whistles.

The atomiser can be used in a spray or flash drying apparatus, or spray coagulation apparatus. More details of methods of spray drying etc may be obtained from, for example, *The Theory and Practice of Industrial Pharmacy*, $3^{rd}$ Edition, Ch.3, p.61, and Ch.13, p.426, Ed: L. Lachman, H.A. Lieberman and J.L. Kanig, Lea & Febiger, 1986, Philadelphia; and *Spray Drying Handbook*, $5^{th}$ Edition, K. Masters, Longman Scientific & Technical 1991; and references therein.

The conditions of operation of the apparatus and storage of the solution (e.g. pH and temperature) should clearly not be such as to degrade the flavouring agent, or introduce impurities, or biological contamination, into the polysaccharide entrapped flavouring agent.

The polysaccharide entrapped flavouring agents used in the compositions according to the invention preferably contain up to 50%, more preferably up to 30%, e.g. 10 to 25% w/w flavouring agent, as measured by steam distillation [British Pharmacopoeia (1988) Appendix 11, Test E: Volatile Oil in Drugs].

The particulate polysaccharide entrapped flavouring agent having a mass median diameter (MMD) in the range 10 to 200 μm has a size distribution such that the delivery of flavouring agent to the lung is minimised and delivery of flavouring agent to the mouth is maximised. We prefer the particulate flavouring agent to have a MMD in the range 10 to 100 μm. We particularly prefer the particulate flavouring agent to have a MMD of greater than 20 μm, e.g. 20 to 70

μm. We prefer less than 5% w/w, and more preferably less than 2% w/w, of the particulate flavouring agent to have a particle size of less then 10 μm. The operating conditions of the atomisation process used to produce the particulate flavouring agent may be controlled so as to produce the desired particle size distribution, alternatively the flavouring agent may be sieved or otherwise classified after production, using for example an "Alpine" Air-Jet Sieve, in order to obtain the desired particle size distribution.

The mass median diameter, as is known by those skilled in the art, is defined such that 50% by mass of the particulate material is in the form of particles having a s smaller diameter. Throughout this specification, the term is used to indicate the mass median diameter as determined by laser diffraction light scattering techniques. The use of other methods of particle sizing may give results which differ somewhat from those obtained by the light scattering technique. Other suitable methods of particle sizing will be well known to those skilled in the art and include microscopy and sedimentation. More details of methods of particle size determination may be obtained from, for example, *The Theory and Practice of Industrial Pharmacy*, $3^{rd}$ Edition, Ch.2, p.21, Ed: L. Lachman, H.A. Lieberman and J.L. Kanig, Lea & Febiger, 1986, Philadelphia, and references therein.

The amount of particulate polysaccharide entrapped flavouring agent present in the compositions according to the invention will obviously depend upon the ability of the flavouring agent to mask the taste of the particular active ingredient employed. However, in general, we prefer the compositions to comprise up to 25% w/w, preferably up to 10% w/w, e.g. 1 to 10% w/w; and more preferably up to 5% w/w, e.g. 1 to 5% w/w, of particulate flavouring agent.

In addition to the particulate flavouring agent the formulations according to the invention may also contain other ingredients such as sweetening agents or colourants. Any conventional sweetening agents may be used but we particularly prefer saccharin sodium, mannitol, aspartame, cyclamates or sugar. When the formulation also contains other ingredients such as a sweetening agent, it may be spray dried into the polysaccharide or mixed with a solution of the polysaccharide before spray drying. Alternatively, if a solid form of a sweetening agent is used it may be admixed with the composition during formulation.

We prefer that at least 80% by weight and preferably more than 90%, of the inhalation medicament particles for use in the compositions according to the invention are of less than 20 μm, more preferably of less than 10 μm, and especially of less than 7 μm in diameter. We particularly prefer at least 80% of the particles to be from 2 to 15 μm in diameter.

The particulate inhalation medicaments may be prepared by any suitable technique, as will be known by those skilled in the art, suitable techniques include milling, using e.g. a hammer mill, micronisation, spray drying and freeze drying.

Medicaments for use in the compositions according to the invention include any medicaments which are conventionally administered by inhalation. Such medicaments include drugs for use in the prophylactic or remedial treatment of reversible obstructive airways disease. Specific medicaments which may be mentioned include salts of cromoglycic acid, e.g. sodium cromoglycate; salts of nedocromil, e.g. nedocromil sodium; inhaled steroids such as beclomethasone dipropionate, tipredane, budesonide and fluticasone; anticholinergic agents such as ipratropium bromide; bronchodilators, e.g. salmeterol, salbutamol, reproterol, terbutaline, isoprenaline and fenoterol, and salts thereof; enzymes; vitamins and antihistamines. If desired a mixture of medicaments, for example a mixture of sodium cromoglycate and a bronchodilator, such as isoprenaline, terbutaline, fenoterol, reproterol or a salt of any one thereof, may be used. We particularly prefer the medicament to be a mixture of sodium cromoglycate and reproterol hydrochloride.

The invention may be particularly useful for medicaments which have unpleasant tastes and/or aromas, or which have no discernable taste of their own.

According to a further aspect of the present invention we provided a method of treatment of reversible obstructive airways disease, which method comprises administration to a patient suffering from or susceptible to such a condition of a pharmaceutical composition comprising a therapeutically effective amount of a particulate inhalation medicament having a mass median diameter in the range 0.01 to 15 μm and a particulate polysaccharide entrapped flavouring agent having a mass median diameter in the range 10 to 200 μm.

The pharmaceutical compositions according to the invention will generally be manufactured in a form suitable for direct administration to a patient. For example, the compositions may comprise the particulate inhalation medicament and flavouring agent in admixture with a solid pharmaceutically acceptable carrier. The carrier preferably has an effective particle size of from 30 to 120 μm.

The term "effective particle size" is used to denote the apparent particle size of a body without distinction as to the number of individual particles which go to make up that body i.e. no distinction is made between a single particle of given size and an agglomerate of the same size which is composed of finer individual particles.

The solid pharmaceutically acceptable carrier in the composition will generally be a non-toxic material chemically inert to the inhalation medicament but may, if so desired, also comprise larger particles of the inhalation medicament. Examples of carriers which may be used in the composition include a dextran, mannitol and, preferably, lactose. A particularly preferred carrier is crystalline lactose.

The particles of carrier preferably have a mass median diameter of from about 30 to 150 μm. The mass median diameter is preferably less than 100 μm and more preferably less than 80 μm. It is particularly preferred that the mass median diameter of the carrier particles be in the range 30 to 80 m, e.g. about 50 to 60 μm.

When the composition is in admixture with a solid carrier, we prefer the content of the inhalation to be from 0.1 to 70% w/w, more preferably from 0.1 to 55% w/w, and especially from 5 to 50% w/w.

Therefore, according to a further, preferred aspect of the invention there is provided a pharmaceutical inhalation composition comprising 0.1 to 70% w/w of a particulate inhalation medicament having a mass median diameter in the range 0.01 to 15 μm and 0.1 to 10% w/w of particulate maltodextrin entrapped peppermint oil having a mass median diameter in the range 10 to 200 μm, in admixture with a solid pharmaceutically acceptable carrier having an effective particle size of from 30 to 120 μm.

The particulate carrier may be prepared by grinding the carrier and subsequently separating out the desired fraction by conventional methods, e.g. by air classification and sieving.

The composition may be prepared by mixing the ingredients together in a mixer, e.g. a planetary or other stirred mixer. The invention thus also provides a method for preparing a composition according to the invention which comprises mixing together the particulate inhalation medicament, the particulate flavouring agent and the solid carrier, after comminution and particle size classification of the ingredients if this is necessary. The technique of Differential Scanning Calorimetry may be used to illustrate the chemical compatibility of the various components of the compositions according to the invention upon storage.

The compositions according to the invention may also be formulated as a so-called "pelletised" composition, i.e. as soft pellets of diameter greater than 30 μm, each pellet comprising a plurality of individual particles loosely held together such that upon inhalation the pellets disintegrate to the constituent particles. Pelletised compositions may be prepared according to the method described in GB 1520247. When the composition is in the form of, e.g. soft pellets, we prefer the content of the inhalation medicament to be from 5 to 99% w/w.

We prefer the compositions according to the invention to have a dispersion of from 5 to 35%, preferably from 10 to 35%, more preferably from 20 to 35% as measured by apparatus B as specified in the British Pharmacopoeia (1988).

The particular formulation and method of putting up the compositions according to the invention will, of course, depend upon the nature of the inhalation device intended for administration of the composition.

The compositions according to the invention may be put up in unit dose form, for example, in gelatine, plastics or other capsules; or in a blister pack as disclosed in GB 2169265 or GB 2246299.

Compositions put up in capsules may be administered from, e.g. the device known as SPINHALER™ (Fisons plc) inhalation device, and compositions put up in blister packs may be administered from, e.g. the device disclosed in GB 2129691 or GB 2246299.

The amount of inhalation medicament contained in a unit dose will, of course, to some extent depend on the desired dosage and the potency of the medicament, but will generally be from about 10μg to 50 mg, e.g. 20 mg.

Therefore, according to a further aspect of the invention, we provide pharmaceutical composition according to the invention in unit dose form comprising from 10 μg to 50 mg of particulate inhalation medicament.

The compositions may also be put up in a multi-dose form, for example, in a cartridge, or a reservoir e.g. a hopper, intended to feed the dosing system of a multi-dose medicament inhalation device such as that disclosed in WO 91/13646.

We prefer the moisture content of the composition put up in this manner to be sufficiently low for the powder to be free flowing. When the composition is intended for administration from, for example, a gelatine capsule we prefer the moisture content to be sufficiently high to prevent the gelatine capsule from becoming brittle.

The compositions according to the invention may also be formulated as medicament compacts, of the type disclosed in EP-A-407028. The compositions are surprisingly advantageous for formulation in this manner since the polysaccharide entrapped flavouring agents are sufficiently resilient to sustain the compression forces required to produce the medicament compacts without releasing the flavouring agent entrapped therein to any significant extent.

The compositions according to the invention are advantageous in that they may mask or otherwise improve the taste of otherwise unpleasant-tasting medicaments, or they may give the composition a recognisable flavour so that the patient realises when a dose has been inhaled. In addition they may exhibit increased dispersion or increased shelf-life when compared to compositions containing other or no flavouring agents. When then compositions according to the invention are put up into, for example, gelatin capsules, they may prevent the capsule becoming brittle, or reduce moisture ingress in to the capsule as compared to compositions containing other or no flavouring agents.

The invention is illustrated, but in no way limited, by the following Examples.

EXAMPLE 1

| Ingredients | % w/w |
| --- | --- |
| Sodium cromoglycate (micronised) | 47.06 |
| Reproterol hydrochloride | 3.53 |
| Flavoured polyglucose | 2.35 |
| (85% maltodextrin:15% peppermint oil) | |
| Lactose | to 100 |

The medicaments, flavouring agent and carrier were each passed through a 44 mesh sieve to remove or break up agglomerated particles, then mixed together using a high energy TURBULA™ mixer. The composition was then put up into hard gelatine capsules each containing 20 mg of sodium cromoglycate (measured as anhydrous) and 1.5 mg of reproterol hydrochloride.

EXAMPLE 2

| Ingredients | % w/w |
| --- | --- |
| Nedocromil sodium (milled) | 50 |
| Flavoured polysaccharide | 5 |
| (85% maltodextrin:15% peppermint oil) | |
| Lactose | to 100 |

The composition was put up into gelatine capsules each containing 10 mg of nedocromil sodium (measured as anhydrous material).

EXAMPLE 3

As for Example 2 but containing 10% w/w flavoured polysaccharide.

EXAMPLE 4

| Ingredients | % w/w |
| --- | --- |
| Nedocromil sodium (milled) | 50 |
| Flavoured polysaccharide | 5 |
| (85% maltodextrin:15% peppermint oil) | |
| Saccharin sodium | 1.25 |
| Lactose | to 100 |

The composition was put up into gelatine capsules each containing 10 mg of nedocromil sodium (measured as anhydrous material).

EXAMPLE 5

As for Example 4 but containing 10% w/w flavoured polysaccharide.

EXAMPLE 6

| Ingredients | % w/w |
| --- | --- |
| Nedocromil sodium (milled) | 50 |
| Flavoured polysaccharide | 5 |
| (85% maltodextrin:15% peppermint oil) | |
| Lactose | to 100 |

The ingredients were mixed according to the method of Example 1, then metered into the powder chamber of a device such as that disclosed in EP-A-407028. The powder was then compacted using a compression rig. The composition when administered by a device as disclosed in EP-A-407028, delivers 6 mg of nedocromil sodium (measured as anhydrous material) per actuation.

The following compositions were prepared according to the method of Example 6:

EXAMPLE 7

As for Example 6 but containing 10% w/w flavoured polysaccharide.

EXAMPLE 8

| Ingredients | % w/w |
| --- | --- |
| Nedocromil sodium (milled) | 50 |
| Flavoured Polysaccharide | 5 |
| (85% maltodextrin:15% peppermint oil) | |
| Saccharin sodium | 1.25 |
| Lactose | to 100 |

EXAMPLE 9

As for Example 8 but containing 10% w/w flavoured polysaccharide.

We claim:

1. A non-pressurised pharmaceutical inhalation composition comprising a therapeutically effective amount of a particulate inhalation medicament having a mass median diameter in the range 0.01 to 15 μm and a particulate polysaccharide entrapped flavouring agent having a mass median diameter in the range 10 to 200 μm.

2. A pharmaceutical composition according to claim 1, wherein the polysaccharide is a polyglucose.

3. A pharmaceutical composition according to claim 2, wherein the polyglucose is maltodextrin.

4. A pharmaceutical composition according to claim 1, wherein the particulate polysaccharide entrapped flavouring agent has a mass median diameter in the range 20 to 70 μm.

5. A pharmaceutical composition according to claim 1, wherein the flavouring agent is peppermint oil.

6. A pharmaceutical composition according to claim 1, which contains one or more medicaments selected from the group consisting of nedocromil sodium, reproterol hydrochloride and sodium cromoglycate.

7. A pharmaceutical composition according to claim 1, in admixture with a solid pharmaceutically acceptable carrier.

8. A pharmaceutical composition according to claim 7, wherein the pharmaceutically acceptable carrier is lactose.

9. A pharmaceutical inhalation composition comprising 0.1 to 70% w/w of a particulate inhalation medicament having a mass median diameter in the range 0.01 to 15 μm and 0.1 to 10% w/w of particulate maltodextrin entrapped peppermint oil having a mass median diameter in the range 10 to 200 μm, in admixture with a solid pharmaceutically acceptable carrier having an effective particle size of from 30 to 120 μm.

10. A pharmaceutical composition according to claim 1, in unit dose form comprising from 10 μg to 50 mg of particulate inhalation medicament.

* * * * *